US005525617A

United States Patent [19]

Hartman et al.

[11] Patent Number: 5,525,617

[45] Date of Patent: Jun. 11, 1996

[54] FIBRINOGEN RECEPTOR ANTAGONISTS

[75] Inventors: George D. Hartman, Lansdale; Melissa S. Egbertson, Ambler; Laura Birchenough, North Wales; Laura Vassallo, Havertown, all of Pa.

[73] Assignee: Merck & Co., Inc., Rahway, N.J.

[21] Appl. No.: 295,316

[22] Filed: Aug. 24, 1994

[51] Int. Cl.[6] ........................ A61K 31/445; A61K 31/40; C07D 211/06; C07D 207/09

[52] U.S. Cl. .......................... 514/319; 514/428; 546/205; 548/567

[58] Field of Search .................................... 514/319, 428; 546/205; 548/567

[56] References Cited

U.S. PATENT DOCUMENTS

| | | | |
|---|---|---|---|
| 4,069,326 | 1/1978 | Teulon | 560/51 |
| 4,647,559 | 3/1987 | Kuhla | 514/212 |
| 5,227,490 | 7/1993 | Hartman et al. | 514/317 |
| 5,264,420 | 11/1993 | Duggan et al. | 514/19 |
| 5,272,158 | 12/1993 | Hartman et al. | 514/323 |
| 5,274,098 | 12/1993 | Stuer | 546/226 |
| 5,281,585 | 1/1994 | Duggan et al. | 514/79 |
| 5,292,756 | 3/1994 | Duggan et al. | 514/331 |
| 5,294,616 | 3/1994 | Duggan et al. | 514/255 |
| 5,321,034 | 6/1994 | Duggan et al. | 514/323 |

FOREIGN PATENT DOCUMENTS

| | | |
|---|---|---|
| 0479481A2 | 4/1992 | European Pat. Off. . |
| 2271567 | 4/1994 | United Kingdom . |
| 94/08962 | 4/1994 | WIPO . |
| 94/08577 | 4/1994 | WIPO . |

*Primary Examiner*—Ceila Chang

*Attorney, Agent, or Firm*—Richard S. Parr; Melvin Winokur

[57] ABSTRACT

Fibrinogen receptor antagonists having the formula

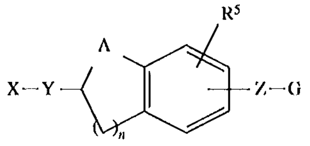

for example

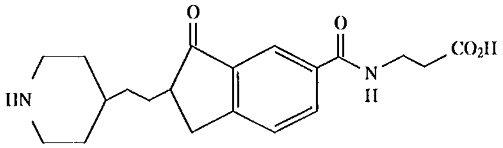

6 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science,* 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripepride arginine-glycine-aspartic acid (RGD) as their glycoprotein IIb/IIIa recognition site. These arginine-glycine-aspartic acid containing tripeprides are recognized by at least one member of a family of structurally related receptors, integrins, which are heterodimeric proteins with two membrane-spanning subunits. The authors state that the conformation of the tripepride sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 ( 1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry* 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. The application PCT/US90/02746 describes the use of antibody-poly-peptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991, also discloses the use of peptides and pseudopeptides such as N-amidino-piperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991, discloses linear polypeptide fibrinogen receptor antagonists. Eur. Pat. App. No. 90101404.3 discloses compounds of the $R^1$—A—$(W)_a$—X—$(CH_2)_b$—$(Y)_c$—B—Z—COOR wherein $R^1$ is a guanidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a compound of the formula:

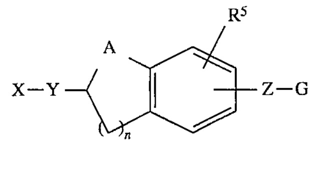

and pharmaceutically acceptable salts thereof, and esters thereof, wherein:

G is

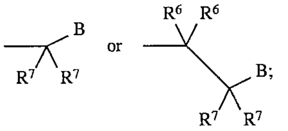

X is

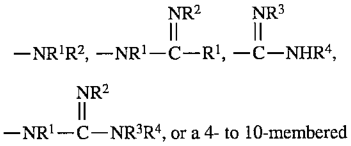

or a 4- to 10-membered mono- or polycyclic aromatic or nonaromatic ring system containing 0, 1, 2, 3 or 4 heteroatoms selected from N, O and S, said heteroatom either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl,
aryl $C_{0-8}$ alkyl,
oxo,
thio,
amino $C_{0-8}$ alkyl, $C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy and
hydroxy $C_{0-6}$ alkyl;

Y and Z are independently chosen from:

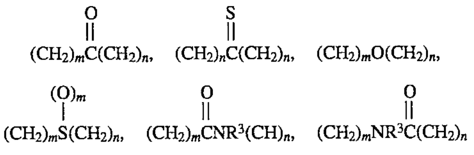

-continued $(CH_2)_mSO_2NR_3(CH_2)_n$, $(CH_2)_mNR_3SO_2(CH_2)_n$,

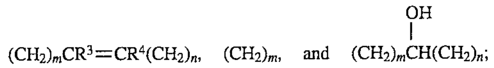

A is chosen from:

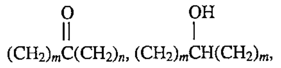

$(CH_2)_m$, and $(CH_2)_mCHR^1(CH)_n$;

$R_5$ is
hydrogen,
$C_{1-6}$ alkyl,
$C_{0-6}$ alkylcarboxy $C_{0-6}$ alkyl,
$C_{0-6}$ alkyloxy $C_{0-6}$ alkyl,
hydroxy $C_{0-6}$ alkyl,
aryl $C_{0-6}$ alkyl, or
halogen;

$R^6$ is
hydrogen,
$C_{1-8}$ alkyl,
aryl $C_{0-6}$ alkyl,
$C_{3-8}$ cycloalkyl $C_{0-6}$ alkyl,
$C_{0-6}$ alkylcarboxy $C_{0-6}$ alkyl,
carboxy $C_{0-6}$ alkyl,
$C_{1-4}$ alkyloxy $C_{0-6}$ alkyl, or
hydroxy $C_{0-6}$ alkyl, provided that any of which groups may be substituted, or unsubstituted independently with $R^1$ or $R^2$, and provided that, when two $R^6$ groups are attached to the same carbon, they may be the same or different;

$R^7$ is
hydrogen, fluorine,
$C_{1-8}$ alkyl,
aryl $C_{0-6}$ alkyl,
$C_{3-8}$ cycloalkyl $C_{0-6}$ alkyl,
$C_{0-6}$ alkyloxy $C_{0-6}$ alkyl,
$C_{0-6}$ alkylamino $C_{0-6}$ alkyl,
carboxy $C_{0-6}$ alkyl,
$C_{0-6}$ dialkylamino $C_{0-6}$ alkyl,
aryl $C_{0-6}$ alkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{0-6}$ alkylcarbonyl $C_{0-6}$ alkyl,
$C_{1-8}$ alkyloxycarbonylamino $C_{0-8}$-alkyl,
aryl $C_{0-6}$ alkylcarbonyl $C_{0-6}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-6}$ alkylaminocarbonyl $C_{0-6}$ alkyl,
aryl $C_{0-6}$ alkylamino carbonyl $C_{0-6}$ alkyl,
$C_{0-6}$ alkylaminosulfonylamino $C_{0-6}$ alkyl,
aryl $C_{0-6}$ alkylaminosulfonylamino $C_{0-6}$ alkyl,
$C_{0-6}$ alkylamino carbonyloxy $C_{0-6}$ alkyl,
aryl $C_{0-6}$ alkylamino carbonyloxy $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl
aryl $C_{0-6}$ alkylcarbonyl $C_{0-6}$ alkyl,
$C_{1-6}$ alkylthiocarbonylamino $C_{0-6}$ alkyl, or
aryl $C_{0-6}$ alkylthiocarbonylamino $C_{0-6}$ alkyl wherein alkyl groups may be unsubstituted or substituted with one or more substituents selected from $R^1$ and $R^2$, and provided that when two $R^7$ groups are attached to the same carbon atom, they may be the same or different;

n is 0, 1 or 2;

m is 0, 1 or 2; and

B is chosen from:

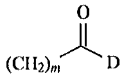

or

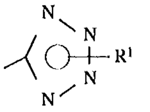

where D is chosen from:

hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, or a naturally occurring L- or D-amino acid joined by an amide linkage and wherein the carboxylic acid moiety of said amino acid is as the free acid or is esterified by $C_{1-6}$ alkyl.

DETAILED DESCRIPTION OF THE INVENTION

The present invention includes compounds having the formula:

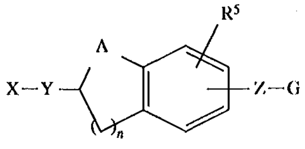

and pharmaceutically acceptable salts thereof, and esters thereof, wherein:

G is

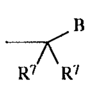

or

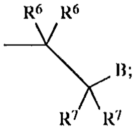

X is

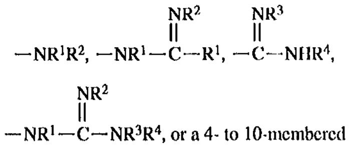

or a 4- to 10-membered mono- or polycyclic aromatic or nonaromatic ring system containing 0, 1, 2, 3 or 4 heteroatoms selected from N, O and S, said heteroatom either unsubstituted or substituted with $R^1$, $R^2$, $R^3$ or $R^4$, wherein $R^1$, $R^2$, $R^3$ and $R^4$ are independently selected from the group consisting of hydrogen, $C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy and hydroxy $C_{0-6}$ alkyl;

Y and Z are independently chosen from:

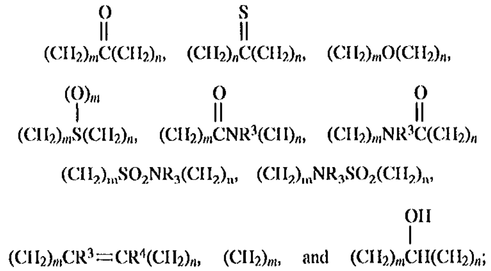

A is chosen from:

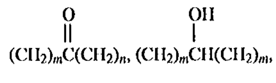

$R^5$ is hydrogen, $C_{1-6}$ alkyl, $C_{0-6}$ alkylcarboxy $C_{0-6}$ alkyl, $C_{0-6}$ alkyloxy $C_{0-6}$ alkyl, hydroxy $C_{0-6}$ alkyl, aryl $C_{0-6}$ alkyl, or halogen;

$R^6$ is hydrogen, $C_{1-8}$ alkyl, aryl $C_{0-6}$ alkyl, $C_{3-8}$ cycloalkyl $C_{0-6}$ alkyl, $C_{0-6}$ alkylcarboxy $C_{0-6}$ alkyl, carboxy $C_{0-6}$ alkyl, $C_{1-4}$ alkyloxy $C_{0-6}$ alkyl, or hydroxy $C_{0-6}$ alkyl, provided that any of which groups may be substituted, or unsubstituted independently with $R^1$ or $R^2$, and provided that, when two $R^6$ groups are attached to the same carbon, they may be the same or different;

$R^7$ is hydrogen, fluorine, $C_{1-8}$ alkyl, aryl $C_{0-6}$ alkyl, $C_{3-8}$ cycloalkyl $C_{0-6}$ alkyl, $C_{0-6}$ alkyloxy $C_{0-6}$ alkyl, $C_{0-6}$ alkylamino $C_{0-6}$ alkyl, carboxy $C_{0-6}$ alkyl, $C_{0-6}$ dialkylamino $C_{0-6}$ alkyl, aryl $C_{0-6}$ alkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{0-6}$ alkylcarbonyl $C_{0-6}$ alkyl, $C_{1-8}$ alkyloxycarbonylamino $C_{0-8}$-alkyl, aryl $C_{0-6}$ alkylcarbonyl $C_{0-6}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-6}$ alkylaminocarbonyl $C_{0-6}$ alkyl, aryl $C_{0-6}$ alkylamino carbonyl $C_{0-6}$ alkyl, $C_{0-6}$ alkylaminosulfonylamino $C_{0-6}$ alkyl, aryl $C_{0-6}$ alkylaminosulfonylamino $C_{0-6}$ alkyl, $C_{0-6}$ alkylamino carbonyloxy $C_{0-6}$ alkyl, aryl $C_{0-6}$ alkylamino carbonyloxy $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl aryl $C_{0-6}$ alkylcarbonyl $C_{0-6}$ alkyl,
$C_{1-6}$ alkylthiocarbonylamino $C_{0-6}$ alkyl, or
aryl $C_{0-6}$ alkylthiocarbonylamino $C_{0-6}$ alkyl
wherein alkyl groups may be unsubstituted or substituted with one or more substituents selected from $R^1$ and $R^2$, and provided that when two $R^7$ groups are attached to the same carbon atom, they may be the same or different:
n independently selected for Y, Z and A, is 0, 1 or 2;
m independently selected for Y, Z, A and B, is 0, 1 or 2; and
B is chosen from:

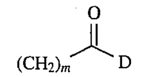 or 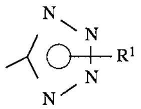

where D is chosen from.:
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy, or
a naturally occurring L- or D-amino acid joined by an amide linkage and wherein the carboxylic acid moiety of said amino acid is as the tree acid or is esterified by $C_{1-6}$ alkyl.

One class of compounds of the invention has the formula

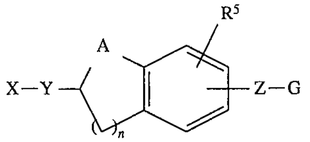

wherein:
X is $-NR^1R^2$ or a 4- to 10-membered mono- or polycyclic aromatic or nonaromatic ring system containing 0, 1 or 2 heteroatoms chosen from N or O, said heteroatom either unsubstituted or substituted with $R^1$ and $R^2$, wherein $R^1$ and R 2 are independently chosen from:
hydrogen,
$C_{1-6}$ alkyl,
aryl $C_{0-6}$ alkyl,
carboxy $C_{0-6}$ alkyl,
hydroxy $C_{0-6}$ alkyl,
$C_{1-3}$ alkyloxy $C_{0-6}$ alkyl, or
amino $C_{0-6}$ alkyl;
Y is
$C_{0-6}$ alkyl,
$C_{1-6}$ alkyl-CO-$C_{0-6}$ alkyl, or
$C_{0-6}$ alkyI-$NR^3$-CO-$C_{0-6}$ alkyl;
A is $(CH_2)_m$, 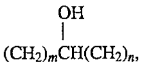, or

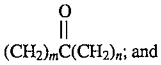; and

G is

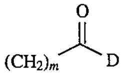

where D is
hydroxy,
$C_{1-6}$ alkyloxy,
aryl $C_{1-4}$ alkyloxy, or
$C_{1-6}$ alkylcarbonyloxy $C_{1-4}$ alkyloxy,
and pharmaceutical salts thereof, and esters thereof.

X, a terminal basic moiety of compounds of the invention, is exemplified by heterocyclic rings such as

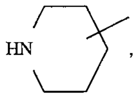, 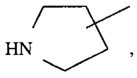, and 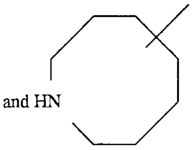

and heteroaromatic rings such as

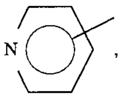, as well as amino, amidino, and guanidino moieties.

The examples describe strategies for preparing compounds where X is a piperidinyl group, using source materials such as

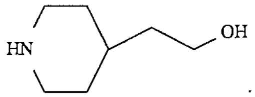.

Similar strategies can be employed for incorporating

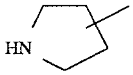

using proline as a source material,

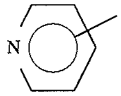

using pyridine-4-carboxylic acid as a source material, and

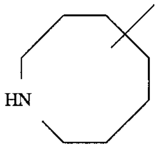 using 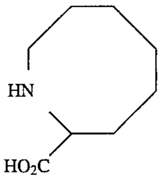

as a source material.

The term "pharmaceutically acceptable salts" means non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, realate, maleate, mandelate, mesylate, methylbromide, methylnitrate, methylsulfate, mucate, napsylate, nitrate, oleate, oxalate, pamaote, palmitate, pantothenate, phosphate/diphosphate, polygalacturonate, salicylate, stearate, subacetate, succinate, tartrate, tartrate, teoclate, tosylate, triethiodide, valerate.

Compounds of the present invention am chiral; included within the scope of the present invention am racemic mixtures and separated enantiomers of the general formula. Furthermore, all diastereomers, including E, Z isomers, of the general formula are included in the present scope. Futhermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" means that amount of a drug or pharmaceutical agent that will elicit the biological or medical response of a tissue, system or animal that is being sought by a researcher or clinician. The term "anti-coagulant" includes agents such as heparin and warfarin. The term "thrombolytic agent" includes agents such as streptokinase and tissue plasminogen activator. The term "platelet anti-aggregation agent" includes agents such as aspirin and dipyridamole.

The term "alkyl" means straight or branched alkane, alkene or alkyne.

The term "aryl" means a 5- or 6-membered aromatic ring containing 0, 1, or 2 heteroatoms selected from O, N, and S.

The terms "alkyloxy" or "alkoxy" include an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

The term "oxy" means an oxygen (O) atom. The term "thio" means a sulfur (S) atom. Under standard nonmenclature used throughout this disclosure, the terminal portion of the designated side chain is described first followed by the adjacent functionality toward the point of attachment. For example, a $C_{1-6}$ alkyl substituted with $C_{1-5}$ alkylcarbonylamino is equivalent to

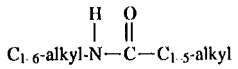

Naturally occurring L- or D-amino acids include, for example, those naturally occurring L-amino acids present in humans, e.g. protein amino acids,, including L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine, and those naturally occurring D-amino acids which are non-protein amino acids, such as those found, for example, in antibiotic substances produced by bacteria and fungi, including D-valine, D-asparagine, D-glutamate, D-ornithine, D-phenylalanine, D-leucine, D-cysteine, and D-aspartate. (see Zubay "BIOCHEMISTRY" Addison-Wesley Publishing Company, Inc. (Reading, Mass.) 1983 pp. 867–870 and Stryer "BIOCHEMISTRY" W. H. Freeman and Company (New York, N.Y.) 3rd Edition 1988 pp. 16–21).

In the schemes and examples below, various reagent symbols have the following meanings:

BOC (or Boc): t-butyloxycarbonyl.
Pd-C: Palladium on activated carbon catalyst.
DMF: Dimethylformamide.
DMSO: Dimethylsulfoxide.
CBZ: Carbobenzyloxy.
$CH_2Cl_2$: Methylene chloride.
$CHCl_3$: Chloroform.
EtOH: Ethanol.
MeOH: Methanol.
EtOAc: Ethyl acetate.
HOAc: Acetic acid.
BOP: Benzotriazol-1-yloxytris(dimethylamino)phosphonium, hexafluorophosphate.
EDC: 1-(3-Dimethylaminopropyl)-3-ethylcarbodiimide hydrochloride.
Oxone: Potassium peroxymonosulfate.
LDA: Lithium diisopropylamide.

The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., *Amer. J. Physiol.,* 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. Intravenously, the most preferred doses will range from about 0.1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those using those forms of transdermal skin patches well known to those of ordinary skill in that art. To be administered in the form of a transdermal delivery system, the dosage administration will, or course, be continuous rather than intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulation agents or thrombolytic agents such as plasminogen activators or streptokinase to achieve synergistic effects in the treatment of various vascular pathologies. They may also be combined with heparin, aspirin, or warfarin.

Examples of this class of compounds are shown in the table below along with $IC_{50}$ data showing inhibition of in vitro aggregation:

TABLE 1

| Compound | $IC_{50}$ |
|---|---|
| 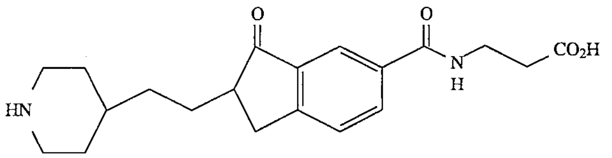 | 2.3 μM |
| 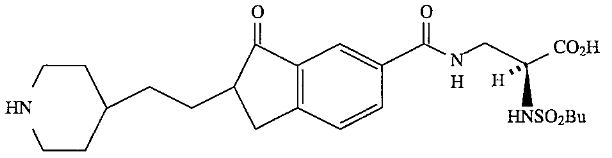 | 9 nM |
| 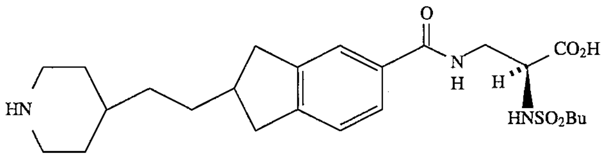 | 14 nM |

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^{2+}$(1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

In addition to the following preparative procedures, several examples of in vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Using methods described herein, as well as others that are known in the literature, the following compounds may be prepared and are descriptive of the present invention:

SCHEME I

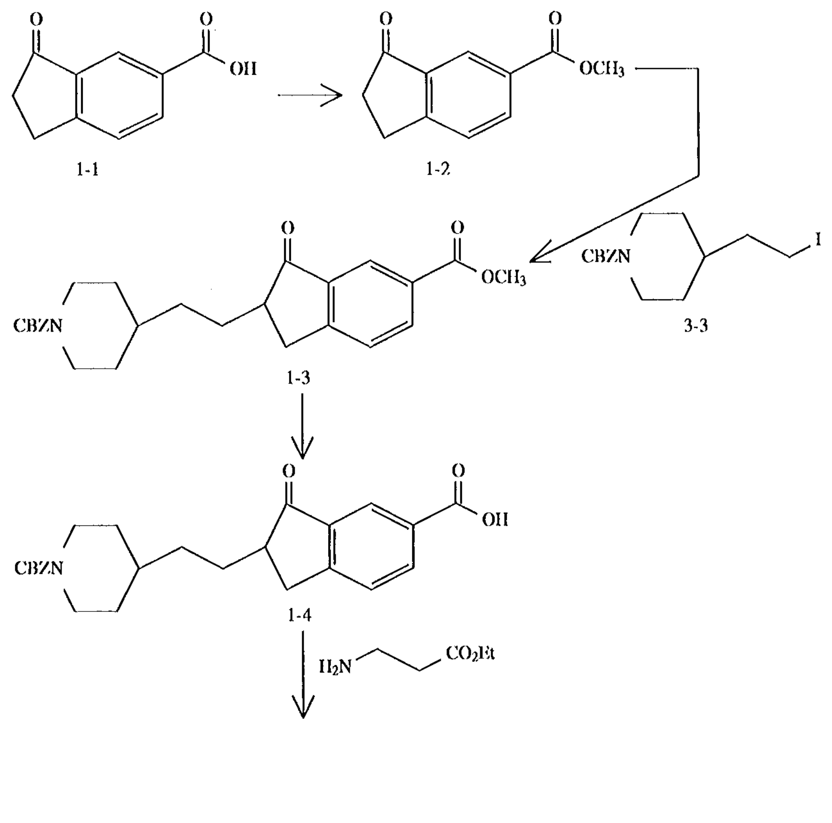

1-1 1-2 1-3 3-3 1-4

-continued

SCHEME I

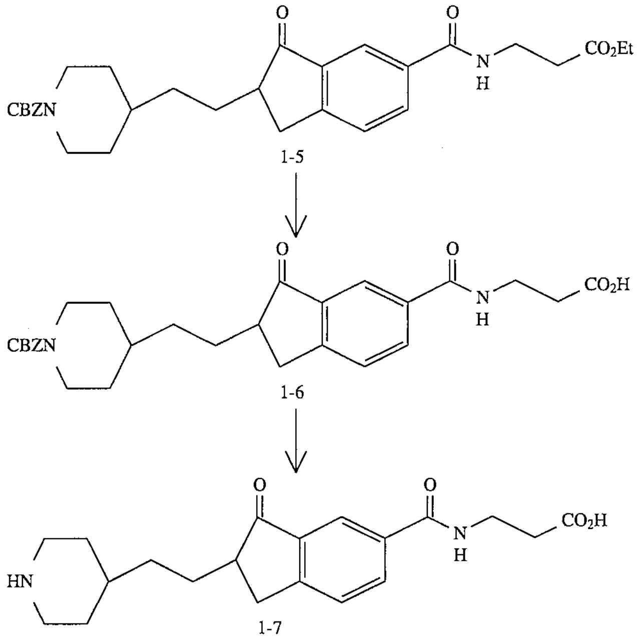

Methyl indan-1-one-6-carboxylate (1-2)

A slurry of 1-1 (*J. Chem. Soc.* 1956, p 4647) (3.5 g, 20 mmol) in $CH_3OH$ (200 mL) was treated with $Cs_2CO_3$ (3.3 g, 10 mmol) for 0.5 h. The homogenous solution was evaporated and the residue was suspended in DMF (200 mL) and treated with methyl iodide (1.2 mL, 20 mmol) at room temperature for 24 h. The solvent was removed in vacuo and the :residue was dissolved in EtOAc and washed with water, saturated $NaHCO_3$, and brine. The EtOAc layer was dried over $MgSO_4$, filtered, evaporated and chromatographed (20% EtOAc/Hexanes) to give 1-2 as a tan solid. Rf (30% EtoAc/Hexanes) 0.48 $^1$H NMR (300 MHz, $CDCl_3$) δ 8.43 (s, 1H), 8.29 (d, 1H), 7.58 (d, 1H), 3.96 (s, 3H), 3.22 (t, 2H), 2.78 (t, 2H).

Methyl 2-[2-(N-Benzyloxycarbonylpiperidin-4-yl)ethyl]indan-1-one-6 -carboxylate (1-3)

A solution of diisopropyl amine (0.9 mL, 6.2 mmol) in THF (15 mL) was cooled to 0° C. and treated with n-Butyl lithium (3.9 mL, 6.2 mmol) for 10 minutes. The solution was cooled to −78° C. and a solution of 1-2 (0.5 g, 2.6 mmol) in THF (5 mL) was added, followed by a solution of 3-3 (1.2 g, 3.1 mmol) in THF (5 mL), and the reaction was stirred at −78° C. for two hours. The reaction was warmed to room temperature, diluted with $H_2O$ and extracted with EtOAc. The organic layer was concentrated and chromatographed (30% EtOAc/Hexanes) to give 1-3 as a yellow oil. Rf (30% EtOAc/Hexanes) 0.4 $^1$H NMR (300 MHz, $CDCl_3$) δ 8.4 (s, 1H), 8.3 (d, 1H), 7.6 (d, 1H), 7.4–7.3 (m, 5H), 5.13 (s, 2H), 4.2 (m, 2H), 3.97 (s, 3H), 3.43 (m, 1H), 2.94 (dd, 1H), 2.85–2.7 (m, 2H), 2.42 (dd, 1H), 2.0 (m, 1H), 1.8–1.0 (m, 8H).

2-[2-(N-Benzyloxycarbonylpiperidin-4-yl)ethyl]indan-1-one-6-carboxylic acid (1-4)

A solution of 1-3 (0.6 g, 1.6 mmol) in 1:1:1 $THF/CH_3OH/H_2O$ (12 mL) was treated with $LiOH·H_2O$ (0.34 g, 8 mmol) at room temperature for 2 h. The solution was diluted with EtOAc and extracted with saturated $NaHCO_3$ solution. The basic aqueous layer was acidified to pH 3–4 with 10% $KHSO_4$ solution and extracted with EtOAc. The organic layers were dried ($MgSO_4$), filtered, and evaporated to give 1-4 as a brown oil. Rf (9:0.5:0.5 $CH_2Cl_2/CH_3OH/HOAc$) 0.36 $^1$H NMR (300 MHz, $CD_3OD$) δ 8.28 (m, 2H), 7.7 (d, 1H), 7.3 (m, 5H), 5.1 (s, 2H), 4.12 (d, 2H), 3.45 (m, 1H), 2.9 (dd, 1H), 2.8 (m, 2H), 2.4 (dd, 1H), 1.7 (bd, 2H), 1.6–1.0 (m, 7H).

2-[2-(N-Benzyloxycarbonylpiperidin-4-yl)ethyl]indan-1-one-6-carbonyl-β-alanine ethyl ester (1-5)

A slurry of 1-4 (0.45 g, 1.2 mmol), β-alanine ethyl ester·HCl (Aldrich) (0.184 g, 1.2 mmol), in $CH_3CN$ (2 mL) was treated with N-methylmorpholine (0.4 mL, 3.6 mmol) and BOP reagent (0.8 g, 1.8 mmol) and stirred at room temperature for 24 h. The solution was diluted with EtOAc, washed with $H_2O$, 10% $KHSO_4$ and brine, dried ($MgSO_4$), filtered, concentrated and chromatographed (30% EtOAc/Hexanes) to give 1-5 as a tan solid. Rf (30% EtOAc/Hexanes) 0.22 $^1$H NMR (300 MHz, $CDCl_3$) δ 8.14 (d, 1H), 8.03 (s, 1H), 7.59 (d, 1H), 7.3 (m, 5H), 6.92 (m, 1H), 5.12 (s, 2H), 4.2–4.1 (m, 4H), 3.75 (dd, 2H), 3.4 (m, 1H), 2.92 (dd, 1H), 2.78 (m, 2H), 2.17 (t, 2H), 2.41 (dd, 1H), 2.0 (m, 1H), 1.7 (m, 3H), 1.6–11 (m, 6H), 1.3 (t, 3H).

2-[2-(N-Benzyloxycarbonylpiperidin-4-yl)ethyl]indan-1-one-6-carbonyl)-β-alanine (1-6)

A solution of 1-5 (0.2 g, 0.43 mmol) was treated as described for 1-4 to give 1-6 as a tan solid. Rf (9:05:0.5 $CH_2Cl_2/CH_3OH/HOAc$) 0.46 $^1$H NMR (300 MHz, $CD_3OD$) δ 8.1 (m, 2H), 7.7 (d, 1H), 7.3 (m, 5H), 5.1 (s, 2H), 4.1 (bd, 2H), 3.63 (t, 2H), 3.45 (m, 1H), 2.90 (dd, 1H), 2.8 (m, 2H), 2.64 (t, 2H), 2.4 (dd, 1H), 2.0 (m, 1H), 1.74 (bd, 2H), 1.6–1.2 (m, 4H), 1.1 (m, 2H).

2-[2-(Piperidin-4-yl)ethyl]indan-1-one-6-carbonyl-β-alanine (1-7)

A solution of ammonium formate (0.425 g, 6.75 mmol) in $CH_3OH$ (15 mL) was treated with 10% Pd/Carbon (0.2 g), and 1-6 (0.2 g, 0.45 mmol) for 20 minutes at room temperature. The reaction mixture was filtered through celite and the filter cake was washed with 10:1:1 $EtOH/H_2O/NH_4OH$. The filtrate was concentrated and chromatographed ($SiO_2$, 10:1:1 $EtOH/H_2O/NH_4OH$) to give 1-7 as a tan solid.

Rf (10:1:1 EtOH/$H_2O$/$NH_4OH$) 0.32 $^1H$ NMR (300 MHz, $CD_3OD$) δ 8.1 (m, 2H), 7.68 (d, 1H), 3.61 (t, 2H), 3.45 (m, 1H), 3.35 (m, 2H), 2.9 (m, 3H), 2.48 (t, 2H), 2.4 (dd, 1H), 2.0 m, 1H), 1.94 (bd, 2H), 1.6 (m, 2H), 1.5–1.35 (m, 4H).
SCHEME II
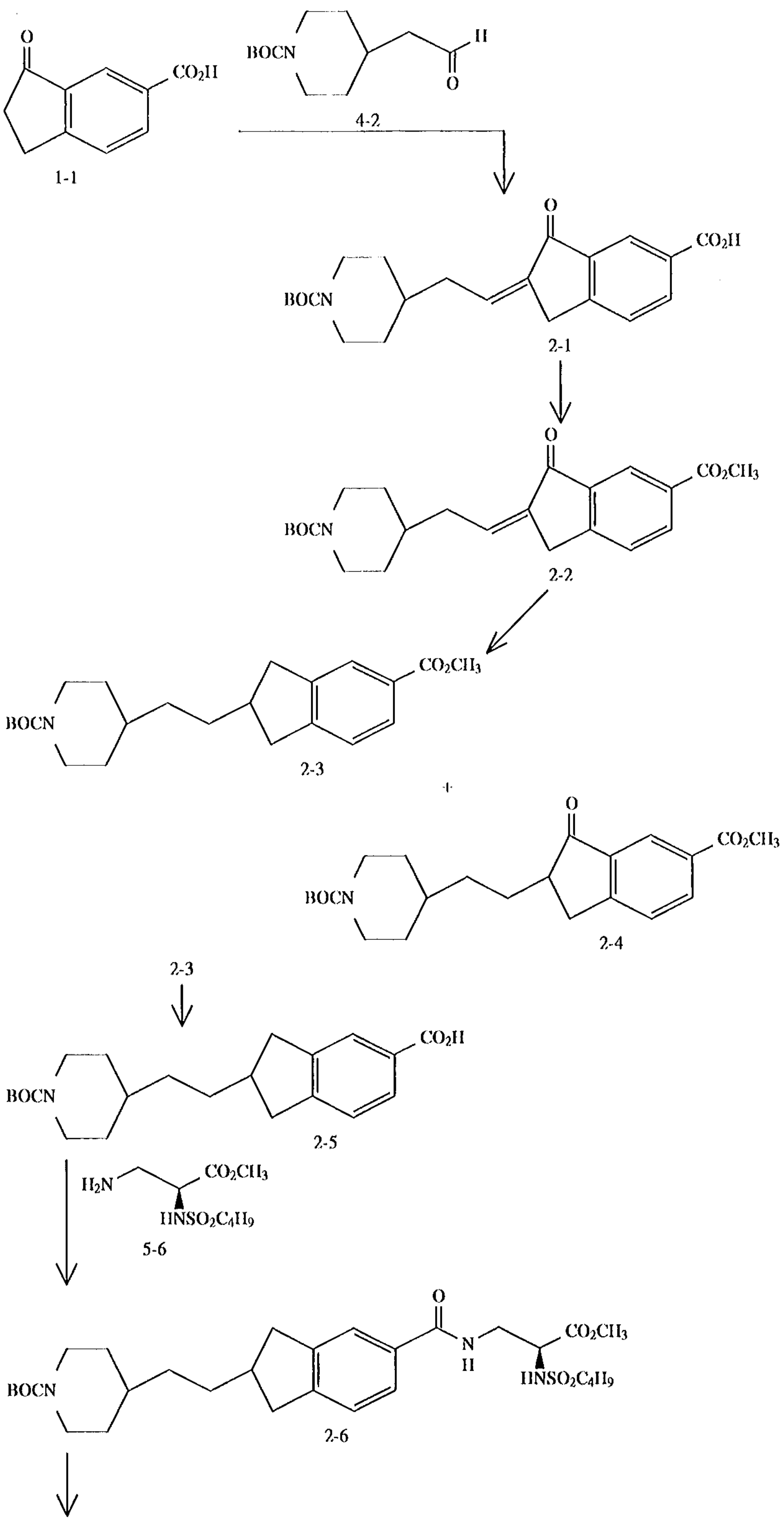

-continued

SCHEME II

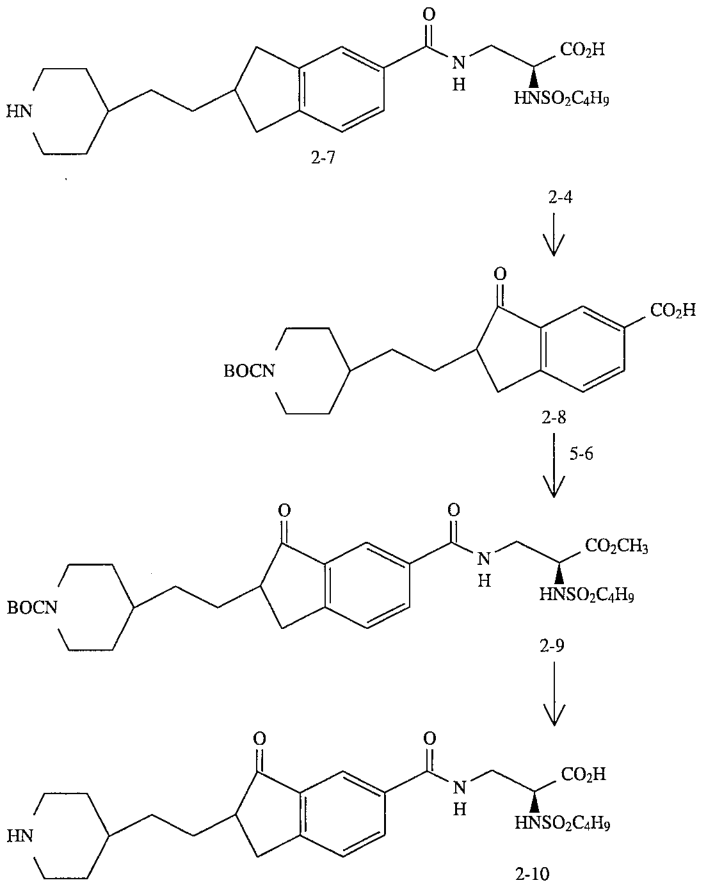

2-7

2-8

2-9

2-10

2-[2-(N-t-Butyloxycarbonylpiperidin-4-yl)ethylidene]indan- 1-one-6-carboxylic acid (2-1)

A solution of diisopropylamine (2.4 mL, 17 mmol) in THF (40 mL) was cooled to 0° C. and treated with n-Butyl lithium (2.01M in Hexanes, 8.5 mL, 17 mmol). After 10 minutes the solution was cooled to −78° C. and 1-1 (1.5 g, 8.5 mmol) was added to give me a slurry. After 25 minutes 4-2 (2.1 g, 9.4 mmol) was added and the reaction was stirred at −78° C. for 1.5 h, when the cooling bath was removed and the reaction warmed for 20 minutes. The reaction was diluted with 10% $KHSO_4$ and EtOAc and extracted. The organic layer was washed with $H_2O$ and brine, dried ($MgSO_4$), filtered and evaporated to give 2-1 as a dark tan oil. Rf (9:0.1:0.1 $CH_2Cl_2/CH_3OH/HOAc$) 0.34 $^1H$ NMR (400 MHz, $CD_3OD$) δ 8.4 (s, 1H), 8.29 (d, 1H), 7.7 (d, 1H), 6.93 (m, 1H), 4.05 (m, 2H), 3.79 (s, 2H), 2.8–2.7 (bs, 2H), 2.33 (t, 2H), 1.8–1.6 (m, 4H), 1.45 (s, 9H), 1.2 (m, 2H).

Methyl 2-[2-(N-t-Butyloxycarbonylpiperidin-4-yl)ethylidene]indan-1 -one-6-carboxylate (2-2)

A slurry of 2-1 (4.5 g, 11.7 mmol) in $CH_3OH$ (120 mL) was treated with $Cs_2CO_3$ (1.9 g, 5.85 mmol) to give a homogenous solution. The solvent was removed in vacuo and the resulting solid was dissolved in DMF (120 mL) and treated with methyliodide (0.72 mL, 11.7 mmol) at room temperature for 18 h. The solution was diluted with EtOAc and washed with $H_2O$, sat. $NaHCO_3$ and brine. The organic layer was dried ($MgSO_4$), filtered, concentrated, and chromatographed (30% EtOAc/Hexanes) to give 2-2 as a white solid. Rf (30% EtOAc/Hexanes) 0.15 $^1H$ NMR (400 MHz, $CDCl_3$) δ 8.52 (s, 1H), 8.28 (d, 1H), 7.58 (d, 1H), 6.94 (m, 1H), 4.1 (bd, 2H), 3.93 (s, 3H), 3.7 (s, 2H), 2.7 (bt, 2H), 2.28 (t, 2H), 1.7 (m, 3H), 1.45 (m, 9H), 1.2 (m, 2H).

Methyl 2-[2-(N-t-Butyloxycarbonylpiperidin-4-yl)ethyl]indane-6-carboxylate (2-3)

Methyl 2-[2-(N-t-Butyloxycarbonylpiperidin-4-yl)ethyl]indan-1-one-6-carboxylate (2-4)

A solution of 2-2 (0.43 g, 1.0 mmol) in $CH_3OH$ (5 mL), under argon was treated with 10% Pd/Carbon (65 mg) and placed under a balloon atmosphere of $H_2$ for 3 h. The solution was filtered and concentrated to give a mixture of indane and alcohol which was dissolved in acetone (5 mL), cooled to −15° C. and treated with Jones reagent ($CrO_3 \cdot H_2SO_4$) dropwise until a dark maroon color was obtained. The solution was neutralized with saturated $NaHCO_3$ solution and extracted with EtOAc. The organic layers were washed with brine, concentrated and the residue was chromatographed using a gradient (10%–30% EtOAc/Hexanes) to give 2-3 and 2-4.

Compound 2-3 Rf (30% EtOAc/Hexanes) 0.91 $^1H$ NMR (400 MHz, $CDCl_3$) δ 7.83 (m, 2H), 7.22 (d, 1H), 4.08 (bd, 2H), 3.89 (s, 3H), 3.06 (dd, 2H), 2.16 (dt, 2H), 2.6 (dd, 2H), 2.42 (m, 1H), 1.68 (bd, 2H), 1.5 (m, 2H), 1.47 (s, 9H), 1.4–1.25 (m, 3H), 1.1 (m, 2H).

Compound 2-4 Rf (30% EtOAc/Hexanes) 0.27 $^1H$ NMR (400 Hz, $CDCl_3$) δ 8.41 (s, 1H), 8.28 (d, 1H), 7.52 (d, 1H), 4.08 (bd, 2H), 3.4 (dd, 1H), 2.35 (dd, 1H), 2.7–2.6 (m, 3,H), 2.0 (m, 1H), 1.67 (bd, 2H), 1.48 (s, 9H), 1.5–1.2 (m, 4H), 1.1 (m, 2H).

2-[2-(N-t-Butyloxycarbonylpiperidin-4-yl)ethyl ]indane-6-carboxylic acid (2-5)

A solution of 2-3 in 1:1:1 THF/$H_2O$/$CH_3OH$ was treated with LiOH·$H_2O$ as described for 1-6 to give 2-5 as a yellow solid. $^1$H NMR (400 MHz, $CD_3OD$) δ 7.8 (m, 2H), 7.24 (d, 2H), 4.4 (1H), 4.04 (bd, 2H), 3.1 (dd, 2H), 2.74 (m, 2H), 2.6 (dd, 2H), 2.45 (m, 1H), 1.7 (bd, 2H), 1.55 (m, 2H), 1.45 (s, 9H), 1.36 (m, 2H), 1.08 (m, 2H).

2-[2-(N-t-Butyloxycarbonylpiperidin-4-yl)ethyl]indan-1-one-6-carboxylic acid (2-8)

A solution of 2-4 in THF/$CH_3OH$/$H_2O$ (1:1:1) was treated with LiOH·$H_2O$ as described for 1-6 to give 2-8 as a tan solid. Rf (9:0.5:0.5 $CH_2Cl_2$/$CH_3OH$/HOAc) 0.44 $^1$H NMR (400 MHz, $CD_3OD$) δ 8.3 (m, 2H), 7.63 (d, 1H), 4.6 (m, 2H), 4.04 (bd, 2H), 3.43 (dd, 1H), 2.9 (dd, 1H), 2.75–2.65 (m, 2H), 1.96 (m, 1H), 1.71 (bd, 2H), 1.5–1.3 (m, 4H), 1.44 (s, 9H), 1.1 (m, 2H).

2-[2-(N-t-Butyloxycarbonylpiperidin-4-yl)ethyl]indan-6-N-[3-(methyl 2(S)-butylsulfonylaminopropionate)]carboxamide (2-6)

A slurry of 2-5 (0.15 g, 0.4 mmol and 5-6 (0.153 g, 0.66 mmol) in $CH_3CN$ (2 mL) was treated with NMM (0.11 mL, 1 mmol) and BOP reagent (0.265 g, 0.6 mmol) to give a homogenous solution, which was stirred at room temperature for 18 hr. The solution was diluted with EtOAc, washed with 10% $KHSO_4$, sat. $NaHCO_3$ and brine and the organic layer was dried ($MgSO_4$) and concentrated. Chromatography (50% EtOAc/Hexanes) gave 2-6 as a white solid. Rf (50% EtOAc/Hexanes) 0.31 $^1$H NMR (300 MHz, $CDCl_3$) δ 7.6 (s, 1H), 7.56 (d, 1H), 7.23 (d, 1H), 6.73 (t, 1H), 5.52 (d, 1H), 4.34 (m, 1H), 4.1 (bd, 2H), 3.91 (m, 1H), 3.84 (s, 3H), 3.80 (m, 1H), 3.08 (m, 4H), 2.7 (t, 2H), 2.6 (m, 2H), 2.43 (m, 1H), 1.83 (m, 2H), 1.7 (d, 2H), 1.5–1.3 (m, 6H), 1.46 (s, 9H), 1.1 (m, 2H), 0.93 (t, 3H).

2-[2-(Piperidin-4-yl)ethyl]indan-6-N-[3-(2(S)-butylsulfonylamnopropionic acid]carboxamide (2-7)

A solution of 2-6 (0.14 g, 0.24 mmol) in 1:1:1 THF/$H_2O$/$CH_3OH$ was treated with LiOH·$H_2O$ as described for 2-5 to give the intermediate Boc-acid. Rf (9:0.5:0.5 $CH_2Cl_2$/$CH_3OH$/HOAc) 0.26 $^1$H NMR (300 MHz, $CD_3OD$) δ 7.62 (s, 1H), 7.59 (d, 1H), 7.23 (d, 1H), 4.3 (dd, 1H), 4.03 (bd, 2H), 3.8 (m, 1H), 3.58 (m, 1H), 3.1–3.0 (m, 4H), 2.71 (5, 2H), 2.6 (dd, 2H), 2.44 (m, 1H), 1.7 (bd, 4H), 1.5 (m, 2H), 1.43 (s, 9H), 1.4–1.3 (m, 4H), 1.06 (m, 2H), 0.86 (t, 3H).

This intermediate acid (0.12 g, 0.21 mmol) was dissolved in EtOAc, cooled to −40° C. and treated with HCl gas. The reaction was warmed to 0° C. for 1 h, then the solvent was removed to give 2-7 as a white solid. Rf (10:1:1 EtOH/$H_2O$/$NH_4OH$) 0.31 $^1$H NMR (300 MHz, $D_2O$) δ 7.49 (s, 1H), 7.43 (d, 1H), 7.2 (d, 1H), 4.2 (dd, 1H), 3.72 (dd, 1H), 3.44 (dd, 1H), 3.75 (bd, 2H), 3.0–2.9 (m, 4H), 2.81 (bt, 2H), 2.46 (dd, 2H), 2.3 (m, 1H), 1.82 (bd, 2H), 1.55–1.45 (m, 4H), 1.4–1.3 (m, 2H), 1.3–1.2 (m, 4H), 1.15 (m, 3H), 0.62 (t, 3H).

2-[2-(N-t-Butyloxycarbonylpiperidin-4-yl)ethyl]indan-1-one-6-N-[3-(methyl 2(S)-butylsulfonylaminopropionate)] carboxamide (2-9)

A solution of 2-8 was treated with 5-6 as described for 2-6 to give 2-9 as a white solid. $^1$H NMR (400 MHz, $CDCl_3$) δ 8.1 (m, 2H), 7.54 (d, 1H), 6.88 (bs, 1H), 5.5 (b, 1H), 4.35 (m, 1H), 4.06 (bd, 2H), 3.94 (m, 1H), 3.83 (s, 3H), 3.8 (m, 1H), 3.37 (dd, 1H), 3.03 (m, 2H), 2.32 (dd, 1H), 2.18 (m, 3H), 1.9 (b, 6H), 1.8 (m, 2H), 1.68 (m, 2H), 1.5 (m, 1H), 1.44 (s, 9H), 1.4 (m, 6H), 1.1 (m, 2H), 0.9 (t, 3H).

2-[2-(Piperidin-4-yl)ethyl]indan-1-one-6-N-[3-(2(S)-butylsulfonylaminopropionic acid]carboxamide (2-10)

A solution of 2-9 (0.06 g, 0.102 mmol) was treated with LiOH as described for 2-5 to give the intermediate Boc-acid. Rf (9:1:1 ($CH_2Cl_2$/$CH_3OH$/HOAc) 0.41 $^1$H NMR (400 MHz, $CD_3OD$) δ 8.13 (m, 2H), 7.62 (d, 1H), 4.3 (dd, 1H), 4.03 (bd, 2H), 3.72 (dd, 1H), 3.6 (m, 1H), 3.42 (dd, 1H), 3.02 (t, 2H), 2.9 (dd, 1H), 2.24 (b, 2H), 1.95 (m, 1H), 1.8–1.7 (m, 4H), 1.6–1.45 (m, 2H), 1.45 (s, 9H), 1.48 (m, 4H), 1.05 (m, 2H), 0.88 (t, 3H).

This intermediate acid was treated with HCl/EtOAc as described for 2-7 to give 2-10 as a white solid. $^1$H NMR (300 MHz, $D_2O$) δ 7.95 (m, 2H), 7.58 (d, 1H), 4.21 (dd, 1H), 3.78 (m, 1H), 3.5 (m, 1H), 3.4–3.3 (m, 3H), 3.0 (t, 2H) 2.9–2.7 (m, 4H), 1.9–1.7 (m, 3H), 1.5 (m, 4H), 1.3–1.1 (m, 5H), 0.6 (t, 3H).

SCHEME III

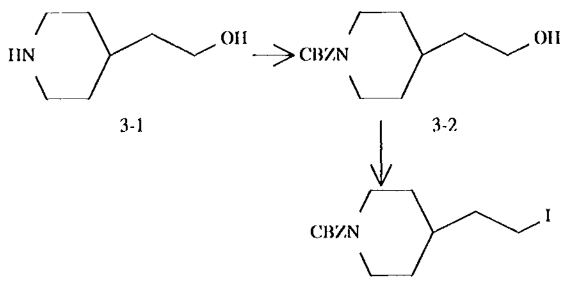

3-1

3-2

3-3

2(N-Benzyloxycarbonylpiperidin-4-yl)ethanol (3-2)

A solution of 3-1 (Aldrich) (25 g, 0.94 mol) in THF (400 mL) was treated with diisopropylethylamine (67 mL, 0.388 mol) and cooled to 0° C. under argon. Benzylchloroformate (27.6 mL, 0.194 mol) was added and the reaction was allowed to warm to room temperature. The reaction was concentrated, the residue was diluted with $Et_2O$ (300 mL), washed with water, 10% $KHSO_4$ solution and brine, dried ($MgSO_4$), filtered and evaporated to give 3-2 as an oil. Rf (35% EtOAc/Hexanes) 0.08 $^1$H NMR (300 MHz, $CDCl_3$) δ 7.38 (s, 5H), 5.13 (s, 2H), 4.18 (b, 2H), 3.7 (dd, 2H), 2.8 (bt, 2H), 1.78 (bd, 2H), 1.5 (m, 2H), 1.4 (m, 1H), 1.2 (m, 2H).

2-(N-Benzyloxycarbonylpiperidin-4-yl)ethyl iodide (3-3)

A solution of 3-2(263 g, 116 mmol) was treated with triphenylphosphine (33.5 g, 128 mmol), imidazole (11.9 g, 175 mmol) and cooled to 0° C. Iodine (32.4 g, 128 mmol) was added and the ice bath was removed. The reaction was filtered into a separatory funnel and the solution was washed with $H_2O$ and brine, dried over $MgSO_4$ and concentrated. The residue was chromatographed (10% EtOAc/Hexanes) to give 3-3 as a colorless oil. Rf (20% EtOAc/Hexanes) 0.56 $^1$H NMR (300 MHz, $CDCl_3$) δ 7.4–7.1 (m, 5H), 5.2–5.05 (bs, 2H), 4.3–4.1 (bs, 2H), 3.2 (t, 2H), 2.8 (bs, 2H), 1.8–1.5 (m, 5H), 1.15 (m, 2H).

SCHEME IV

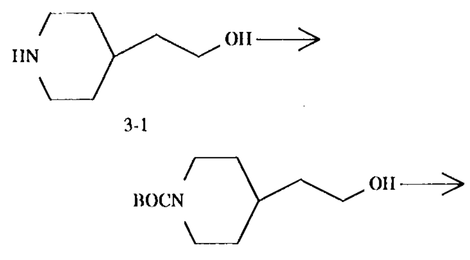

3-1

4-1

-continued

SCHEME IV

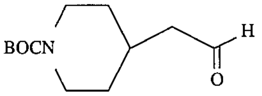

4-2

2(N-t-Butyloxycarbonylaminopiperidin-4-yl)ethanol (4-1)

A solution of 3-1(130 g, 1 mole) in dioxane (700 mL) was cooled to 0° C. and treated with 3N NaOH (40 g in 333 mL $H_2O$) and di-t-butyldicarbonate (222 g, 1 mole). The solution was allowed to warm to room temperature and stirred overnight. The solution was concentrated, diluted with water and $Et_2O$ and extracted. The water layer was extracted several times with $Et_2O$. The $Et_2O$ layers were combined, dried ($MgSO_4$) filtered and evaporated to give 4-1 as a white solid. Rf (1:1 EtOAc/Hexanes) 0.38 $^1$H NMR (300 MHz, $CDCl_3$) δ 4.05 (bd, 2H), 3.7 (m, 2H), 2.68 (bt, 2H), 1.67 (bd, 2H), 1.6–1.45 (m, 3H), 1.45 (s, 9H), 1.12 (m, 2H).

2-(N-t-Butyloxycarbonylpiperidin-4-yl)acetaldehyde (4-2)

A solution of $CH_2Cl_2$ (200 mL) was treated with pyridiniumchlorochromate (PCC) (6.7 g, 0.031 mol) for five minutes. Solid NaOAc (2.55 g, 0.031 mol) and 4Å molecular sieves were added, followed by a solution of 4-1 (4.75 g, 0.02 mol) in $CH_2Cl_2$ (50 mL). The reaction was stirred for 3 h, diluted with 400 mL of $Et_2O$, and filtered through a pad of silica gel. The silica gel was washed with 1 L of $Et_2O$ and 0.5 L of 1:1 $Et_2O/CHCl_3$. The organic solutions were combined, concentrated to give a greenish oil which was filtered through another pad of silica gel, eluting with 1.2 L of $Et_2O$. The filtrate was concentrated to give 4-2 as a yellow oil. $^1$H NMR (300 MHz, $CDCl_3$) δ 9.77 (s, 1H), 4.08 (bd, 2H), 2.7 (bt, 2H), 2.37 (dd, 2H), 2.03 (m, 1H), 1.7 (bd, 2H), 1.42 (s, 9H), 1.2 (m, 2H).

Methyl 2-(S)-benzyloxycarbonylamino-3-aminopropionate hydrochloride (5-2)

To a cooled suspension of 2-(S)-benzyloxycarbonylamino-3-aminopropionic acid 5-1 (10 g, 0.042 mol) in 150 ml of methanol was added 5.47 g (0.046 mol) of thionyl chloride over 20 minutes. The resulting solution was allowed to stir at room temperature overnight. After ~18 hrs, the solvent was removed in vacuo, and the residual solid was stirred with 150 ml of ether for 0.5 hr. The resulting white solid was collected and air dried to give 5-2. $^1$H NMR (300 MHz, $CD_3OD$) δ 3.26 (2H, m), 3.45 ( 1 H, dd), 3.77 (3H, s), 4.25 (1H, m), 5.13 (2H, s), 7.37 (5H, m).

Methyl 2-(S)-benzyloxycarbonylamino-3-(N-t-butyloxycarbonyl)aminopropionate (5-3)

To a 2-phase mixture of $CH_2Cl_2$ (500 ml) and saturated $NaHCO_3$ solution (300 ml) was added 28.87 g (0.10 mol) of 5-2. After a few minutes, 21.83 g (0.10 mol) of di-t-butyldicarbonate was added in one portion and the resulting mixture was stirred at room temperature for 4 hours. The $CH_2Cl_2$ layer was then separated from the aqueous layer, and the aqueous layer was extracted with 300 ml of $CH_2Cl_2$. The combined organic extracts were washed with brine, dried and the solvent removed in vacuo to provide the product as viscous oil. Trituration of this oil with 300 ml of hexane gave 5-3 as a white solid, m.p. 85°–87°. $^1$H NMR (300 MHz, $CDCl_3$) δ 1.42 (9H, s), 1.50 (4H, m), 1.62 (1H, m), 3.52 (2H, m), 3.75 (3H, s), 4.41 (1 H, m), 4.83 (1H, m), 5.12 (2H, s), 5.78 (1H, m), 7.35 (5H, m).

Methyl 2-(S)-amino-3-(N-t-butyloxycarbonyl)aminopropprionate (5-4)

To a solution of 6.60 g (0.0187 mol) 5-3 in 150 ml EtOH was added 0.5 g of 10% Pd/C. The resulting mixture was hydrogenated under balloon pressure at r.t. for 4 hrs. The catalyst was filtered off and the solvent removed in vacuo to provide 5-4 as a viscous oil. $^1$H NMR (300 MHz, $CDCl_3$) δ 1.45 (9H, s), 1.49 (2H, m), 1.59 (2H, m), 3.25 (1H, m), 3.49 (1H, m), 3.58 (1H, m), 3.75 (3H, s), 5.03 (1H, m).

SCHEME V

2-Substituted-3-Aminopropionates are prepared in the following manner:

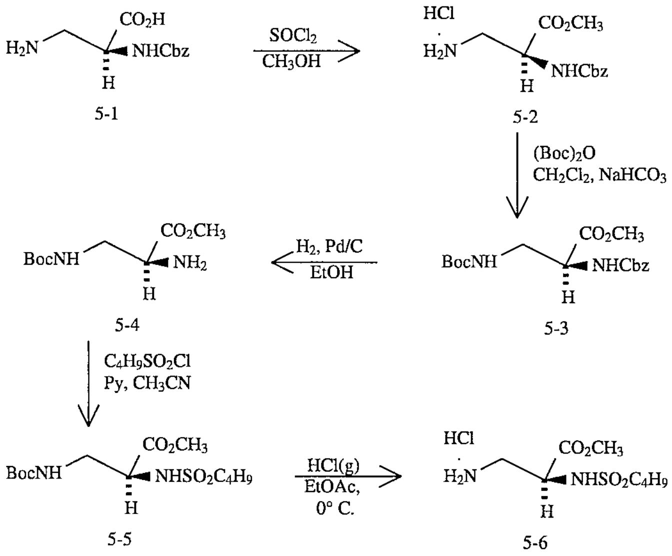

Methyl 2-( S )-butylsulfonylamino-3-(N-t-butylcarbonyl)aminopropionate (5-5)

To a solution of 0.400 g (0.00183 mol) of 5-4 in 10 ml of $CH_3CN$ was added 0.226 g (0.00286 mol) pyridine followed by 0.408 g (0.0026 mol) of n-butanesulfonyl chloride. The solution was stirred at room temperature for 2.5 hrs at which time starting material was consumed. The solvent was removed in vacuo and 50 ml of $H_2O$ added to the residual material. This mixture was extracted with 3×50 ml portions of ethyl acetate and the combined extracts layer was dried ($Na_2SO_4$) filtered and concentrated to give 0.5 g of viscous oil. Trituration to this oil with 25 ml of hexane provided 5-5 as a white, amorphous solid. $^1H$ NMR (300 MHz, $CDCl_3$) δ 0.95 (3H, t), 1.43 (9H, s), 1.48 (2H, m), 1.80 (2H, m), 3.03 (2H, m), 3.52 (2H, t), 3.80 (3H, s), 4.22 (1H, m), 4.99 (1H, bt), 5.48 (1H, bd).

Methyl 2-(S)-butylsulfonylamino-3-aminopropionate hydrochloride (5-6)

A cooled (−20° C.) solution of 0.400 g (0.00118 mol) of 5-5 in 25 ml of ethyl acetate was treated with HCl gas for 15 min. The resulting solution was then stoppered and allowed to stir at 0° C. for an additional hour. The solvent and excess HCl were removed in vacuo to give 5-6 as a hygroscopic, yellowish foam. $^1H$ NMR (300 MHz, $CDCl_3$) δ 0.94 (3H, t), 1.44 (9H, s), 1.48 (2H, m), 1.80 (2H, m), 3.04 (2H, m), 3.53 (2H, bt), 3.80 (3H, s), 4.22 (1 H, m), 4.93 (1H, m), 5.40 (1H, bd).

What is claimed is:

1. A compound having the formula

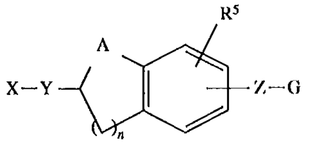

and pharmaceutical salts thereof, and esters thereof, wherein

X is piperidinyl or pyrrolidinyl;

Y is $C_{0-6}$ alkyl, $C_{1-6}$ alkyl-CO-$C_{0-6}$ alkyl, or $C_{0-6}$ alkyl-$NR^3$-CO-$C_{0-6}$ alkyl;

Z is:

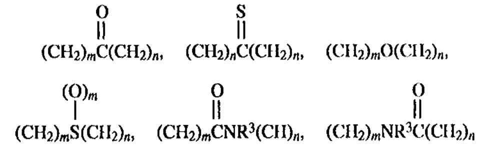

$(CH_2)_mSO_2NR_3(CH_2)_n$, $(CH_2)_mNR_3SO_2(CH_2)_n$, $(CH_2)_mCR^3{=}CR^4(CH_2)_n$, $(CH_2)_m$, and 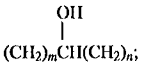

$R^3$ and $R^4$ are independently selected from the group consisting of hydrogen, $C_{1-10}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy and hydroxy $C_{0-6}$ alkyl;

A is chosen from:

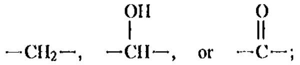

$R^5$ is hydrogen, $C_{1-6}$ alkyl, $C_{0-6}$ alkylcarboxy $C_{0-6}$ alkyl, $C_{0-6}$ alkyloxy $C_{0-6}$ alkyl, hydroxy $C_{0-6}$ alkyl, or halogen;

G is

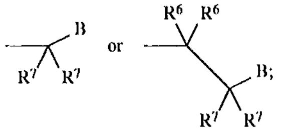

B is chosen from:

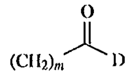

where D is chosen from:

hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, or a naturally occurring L- or D-amino acid joined by an amide linkage and wherein the carboxylic acid moiety of said amino acid is as the free acid or is esterified by $C_{1-6}$ alkyl $R^6$ is hydrogen, $C_{1-8}$ alkyl, $C_{3-8}$ cycloalkyl $C_{0-6}$ alkyl, $C_{0-6}$ alkylcarboxy $C_{0-6}$ alkyl, carboxy $C_{0-6}$ alkyl, $C_{1-4}$ alkyloxy $C_{0-6}$ alkyl, or hydroxy $C_{0-6}$ alkyl;

$R^7$ is hydrogen, fluorine, $C_{1-8}$ alkyl, $C_{3-8}$ cycloalkyl $C_{0-6}$ alkyl, $C_{0-6}$ alkyloxy $C_{0-6}$ alkyl, $C_{0-6}$ alkylamino $C_{0-6}$ alkyl, carboxy $C_{0-6}$ alkyl, $C_{0-6}$ dialkylamino $C_{0-6}$ alkyl, $C_{1-8}$ alkylsulfonylamino $C_{0-6}$ alkyl, $C_{0-6}$ alkylcarbonyl $C_{0-6}$ alkyl, $C_{1-8}$ alkyloxycarbonylamino $C_{0-8}$-alkyl, $C_{1-8}$ alkylcarbonylamino $C_{0-6}$ alkyl, $C_{0-8}$ alkylaminocarbonylamino $C_{0-6}$ alkyl, $C_{0-6}$ alkylaminocarbonyl $C_{0-6}$ alkyl, $C_{0-6}$ aikylaminosulfonylamino $C_{0-6}$ alkyl, $C_{0-6}$ alkylamino carbonyloxy $C_{0-6}$ alkyl, $C_{1-6}$ alkylsulfonyl $C_{0-6}$ alkyl, $C_{1-6}$ alkylcarbonyl $C_{0-6}$ alkyl, $C_{1-6}$ alkylthiocarbonylamino $C_{0-6}$ alkyl, wherein $R^6$ and $R^7$ are optionally substituted with one or more substituents selected from $R^3$ and $R^4$ and wherein, when two $R^6$ groups are attached to the same carbon, they are optionally the same or different, and when two $R^7$ groups are attached to the same carbon, they are optionally the same or different;

n is 0, 1 or 2;

m is 0, 1 or 2.

2. A compound of claim 1 selected from the group consisting of:

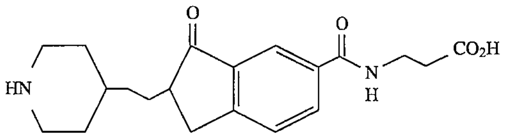

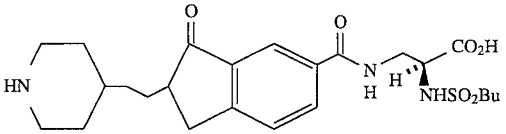

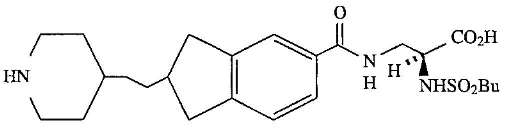

and pharmaceutical salts thereof, and esters thereof.

3. A composition for inhibiting the aggregation of blood platelets in a mammal, comprising a compound of claim 1 and a pharmaceutically acceptable carrier.

4. A composition for inhibiting the aggregation of blood platelets, in a mammal, comprising a compound of claim 2 and a pharmaceutically acceptable carrier.

5. A method for inhibiting the aggregation of blood platelets in a mammal by blocking fibrinogen from acting at its receptor site, comprising administering an antifibrinogenic binding effective amount of a composition of claim 3.

6. A method for inhibiting the aggregation of blood platelets in a mammal by blocking fibrinogen from acting at its receptor site, comprising administering an antifibrinogenic binding effective amount of a composition of claim 4.

* * * * *